(12) United States Patent
Cook

(10) Patent No.: US 6,892,731 B2
(45) Date of Patent: *May 17, 2005

(54) RETAINER FOR LARYNGEAL MASK

(75) Inventor: Daniel J. Cook, Richmond Heights, MO (US)

(73) Assignee: Cookgas ( * ) Notice: Subject to any disclaimer, the term of this patent is extended or adjusted under 35 U.S.C. 154(b) by 0 days.

This patent is subject to a terminal disclaimer.

(21) Appl. No.: 10/072,247

(22) Filed: Oct. 23, 2001

(65) Prior Publication Data
US 2002/0069879 A1 Jun. 13, 2002

Related U.S. Application Data

(60) Continuation of application No. 09/179,928, filed on Oct. 27, 1998, now Pat. No. 6,422,239, which is a division of application No. 08/843,631, filed on Apr. 10, 1997, now Pat. No. 6,937,860.

(51) Int. Cl.$^7$ ............................................. A61M 16/00
(52) U.S. Cl. ............................ 128/207.15; 128/207.14; 128/200.26
(58) Field of Search ................... 128/207.14, 207.15, 128/200.26; 606/80, 83, 79, 108; 411/378, 418, 392, 426; 604/165.01–165.04, 902

(56) References Cited

U.S. PATENT DOCUMENTS

| | | | | |
|---|---|---|---|---|
| 678,814 A | * | 7/1901 | Riggs | 408/219 |
| 1,345,425 A | * | 7/1920 | Wells | 408/219 |
| 2,335,741 A | * | 11/1943 | Contaldi | 408/222 |
| 2,787,010 A | * | 4/1957 | Uphoff | 408/204 |
| 3,606,669 A | * | 9/1971 | Kemble | 29/434 |
| 3,756,601 A | * | 9/1973 | Frey et al. | 473/582 |
| 3,945,069 A | * | 3/1976 | Cecil | 470/198 |
| 4,388,076 A | * | 6/1983 | Waters | 604/165.02 |
| 4,509,514 A | | 4/1985 | Brain | 128/207 |
| RE31,948 E | * | 7/1985 | Deutsch et al. | 433/221 |
| 4,582,056 A | * | 4/1986 | McCorkle, Jr. | 606/1 |
| 4,593,687 A | * | 6/1986 | Gray | 128/200.26 |
| 4,661,028 A | * | 4/1987 | Sanger | 408/165 |
| 4,751,922 A | * | 6/1988 | DiPietropolo | 606/80 |
| 4,863,439 A | | 9/1989 | Sanderson | 604/264 |
| 5,024,220 A | | 6/1991 | Holmgreen et al. | 128/207.18 |
| 5,033,919 A | * | 7/1991 | Choe | 408/217 |
| 5,037,251 A | * | 8/1991 | Roth | 408/222 |
| 5,222,487 A | * | 6/1993 | Carr et al. | 128/200.26 |
| 5,326,196 A | * | 7/1994 | Noll | 408/56 |
| 5,527,316 A | * | 6/1996 | Stone et al. | 606/80 |
| 5,562,371 A | * | 10/1996 | Reed | 408/222 |
| 5,562,673 A | * | 10/1996 | Koblish et al. | 606/80 |
| 5,579,762 A | * | 12/1996 | Lee | 128/207.14 |
| 5,720,749 A | * | 2/1998 | Rupp | 606/79 |
| 6,422,239 B1 | * | 7/2002 | Cook | 128/207.15 |

* cited by examiner

Primary Examiner—Henry Bennett
Assistant Examiner—Mital Patel
(74) Attorney, Agent, or Firm—Ahaji Amos, Esq

(57) ABSTRACT

An endo-tracheal tube retainer used to facilitate the removal of a laryngeal mask of the type used to facilitate lung ventilation and the insertion of endo-tracheal tubes or related medical instruments through a patient's laryngeal opening is provided. The endo-tracheal tube retainer includes a semi-rigid stylet having proximate and distal ends and a soft curved stylet cap secured to the proximal end. The endo-tracheal tube also includes a connection adapter that is tapered from front to rear for secure insertion within a range of endo-tracheal tubes, removably secured to the distal end.

8 Claims, 4 Drawing Sheets

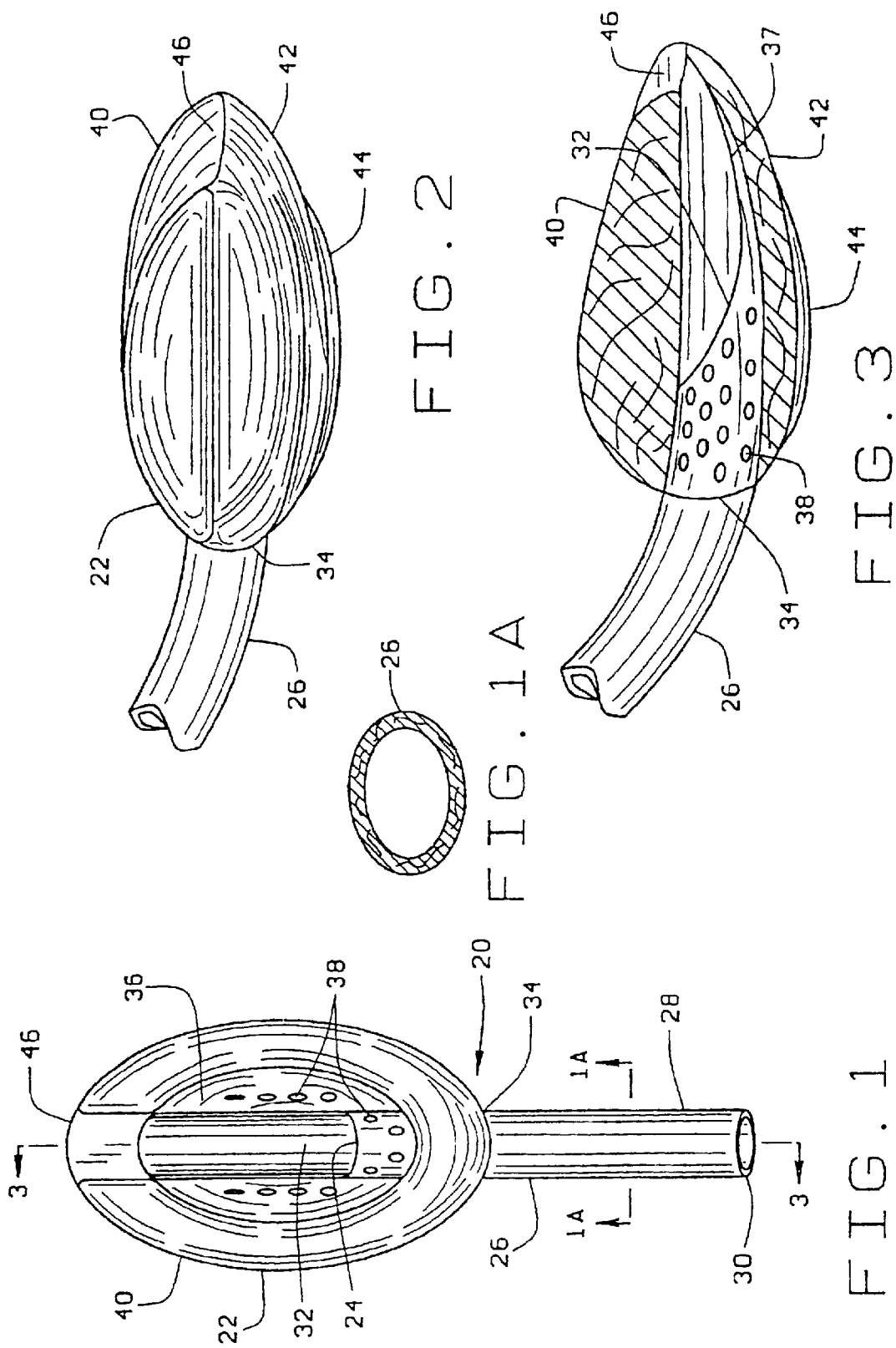

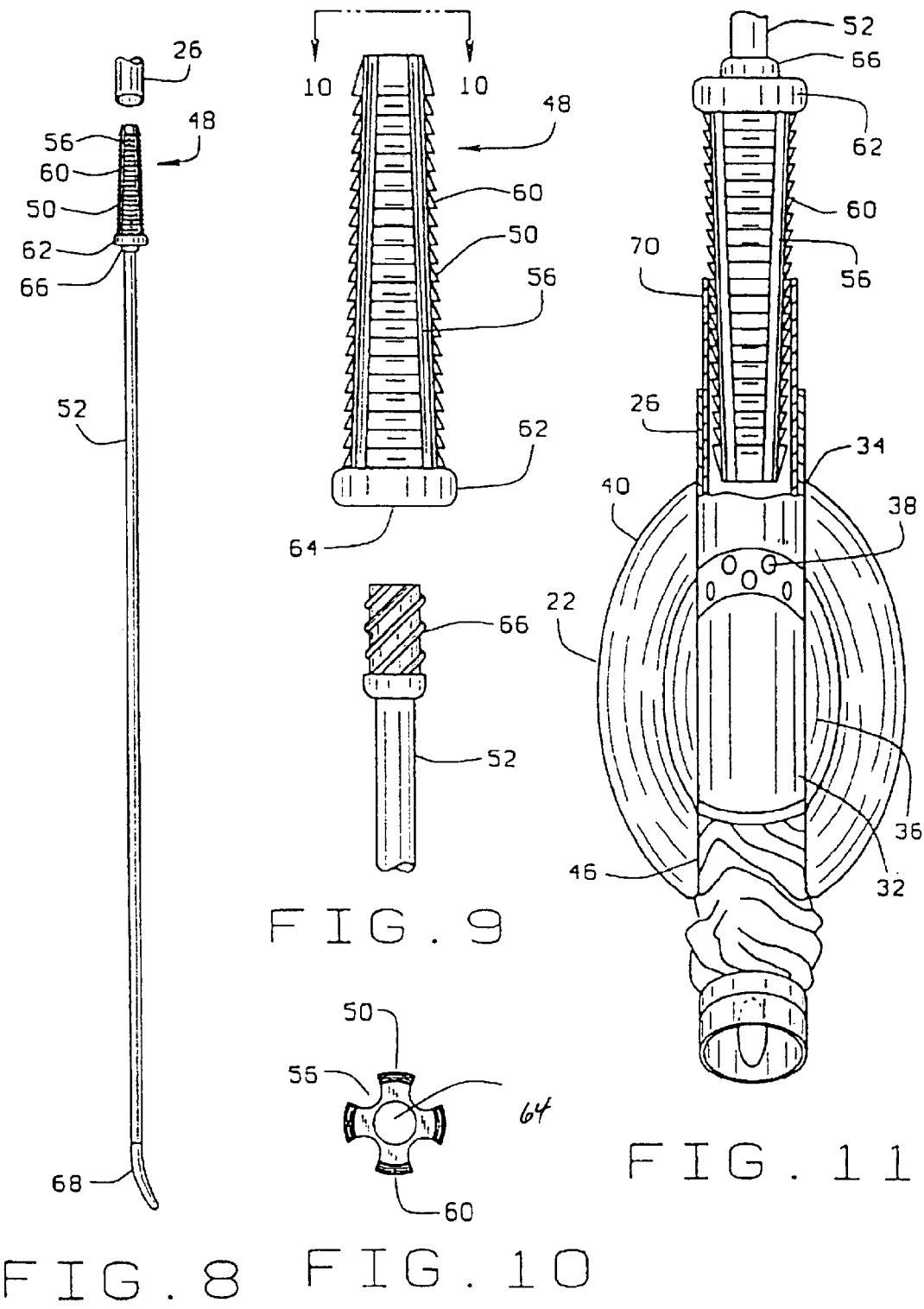

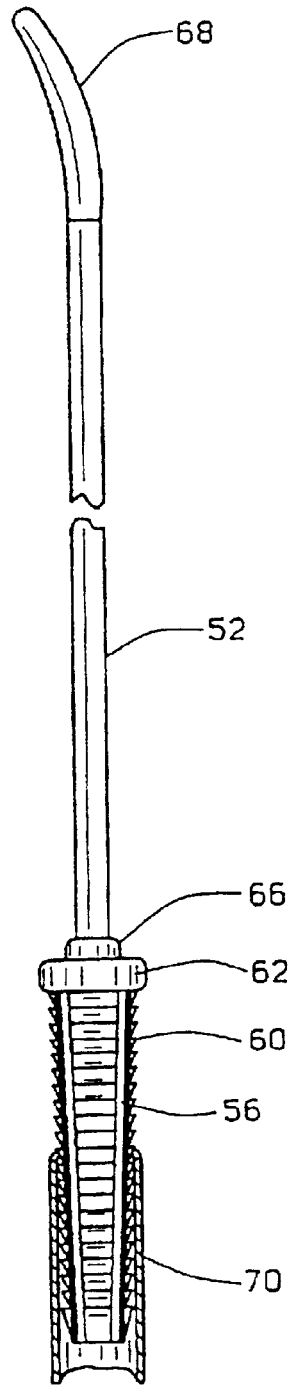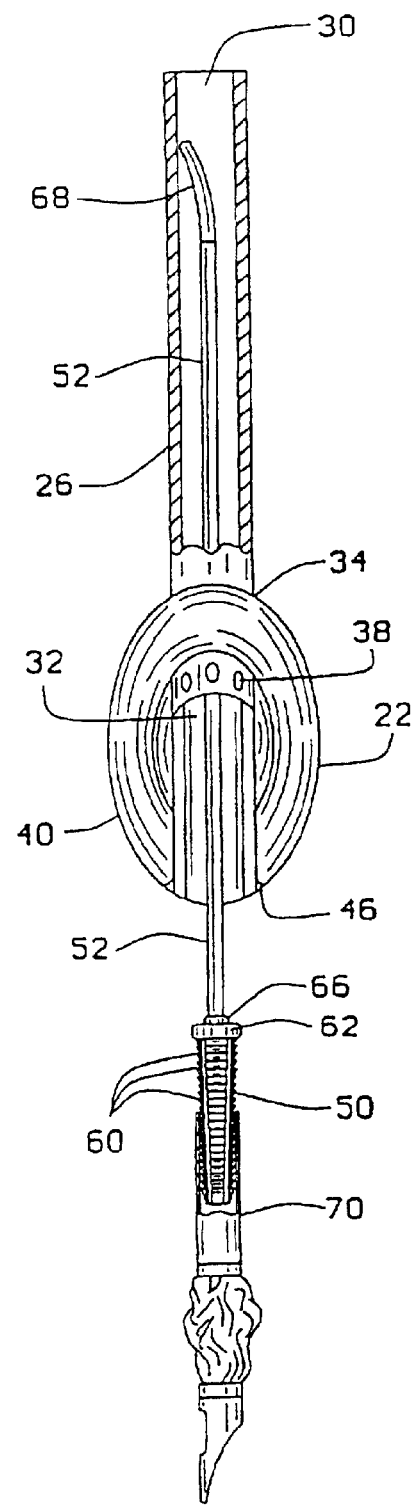
FIG. 12                    FIG. 13

RETAINER FOR LARYNGEAL MASK

CROSS-REFERENCE TO RELATED APPLICATIONS

This is a continuation of U.S. patent application Ser. No. 09/179,928, filed Oct. 27, 1998, now U.S. Pat. No. 6,422,239 which is hereby incorporated by reference in its entirety. U.S. patent application Ser. No. 09/179,928 is a divisional of U.S. patent application Ser. No. 08/843,631, filed Apr. 10, 1997, which issued as U.S. Pat. No. 5,937,860 on Aug. 17, 1999.

STATEMENT REGARDING FEDERALLY SPONSORED RESEARCH OR DEVELOPMENT

Not applicable.

BACKGROUND OF THE INVENTION

This invention relates to an artificial airway device designed to facilitate lung ventilation and the insertion of endo-tracheal tubes or related medical instruments into the laryngeal opening of an unconscious patient. More specifically the invention is directed to a retainer for a laryngeal mask that is designed to be placed within the oropharynx region, over the laryngeal opening, and secured by means of air inflation, thereby sealing the circumference of the laryngeal opening against the aspiration of regurgitated gastric contents, and providing a direct pathway from a point exterior to the oral cavity to the laryngeal opening.

In general, laryngeal masks allowing for both rapid lung ventilation and the insertion of medical instruments and tubes into the laryngeal openings of patients have been described in patents, such as U.S. Pat. No. 4,509,514 to Brain. Consisting of two essential parts, a breathing tube and an inflatable mask, these devices are inserted blindly into a patient's throat, and when properly positioned, terminate at the laryngeal opening. A seal is then formed around the circumference of the laryngeal opening by the inflation of a ring-like structure located on the front of the mask. Inflation of the ring exerts pressure against both the front and rear portions of the oropharynx, securing the device in place such that the laryngeal opening is positioned within a recessed cavity in the mask face. Extending from a point external to the oral cavity, the flexible breathing tube terminates within the recessed cavity, aligned axially with the laryngeal opening. The positioning of the flexible breathing tube allows the passage of small diameter endo-tracheal tubes or related medical instruments into the laryngeal opening, in addition to allowing for lung ventilation.

Current laryngeal masks have several drawbacks in the areas of placement, lung ventilation, and endo-tracheal intubation. For example, during insertion and positioning, the flexible nature of the deflated ring structure and surrounding mask may allow the distal end of the mask to bend back on itself, preventing proper inflation and the formation of a tight seal. Also, once successfully installed, the current mask designs may fail to exert sufficient pressure against the larynx necessary to maintain proper positioning during intubation and ventilation. This is due to the variations in anatomy of the oropharynx region, the muscular tension against which the mask is exerting pressure, and the curvature of the device itself.

During lung ventilation, it is possible for the tip of the epiglottis to become lodged in the distal lumen of the flexible breathing tube, preventing the passage of air or endo-tracheal tubes. This problem is often overcome by the placement of a series of band structures at the entrance to the distal lumen, preventing the epiglottis from entering the breathing tube. However, these band structures severely restrict the size of endo-tracheal tubes and related medical devices which may be passed through the flexible breathing tube. Furthermore, after the insertion of an endo-tracheal tube or related medical device, it often becomes difficult to remove the laryngeal mask from the patient's oropharynx without dislodging or accidentally extracting the endo-tracheal tube or medical device along with the laryngeal mask.

The removable laryngeal mask of the present invention overcomes these problems and is distinguished from the prior art by providing generally the same function as described above, yet allowing a more secure and certain insertion, allowing the unrestricted passage of large diameter endo-tracheal tubes directly to the laryngeal opening, and providing alternate airways to prevent blockage of the flexible breathing tube during patient ventilation.

SUMMARY OF THE INVENTION

Among the several objects and advantages of the present invention include:

The provision of a new and improved laryngeal mask for the facilitation of lung ventilation and the insertion of endo-tracheal tubes and related medical instruments into the laryngeal opening;

The provision of the aforementioned laryngeal mask which, includes a flexible breathing tube portion and an inflatable mask portion, each gently curved along a single arcuate curve for ease of insertion and positioning;

The provision of the aforementioned laryngeal mask which, includes an air-tight seal securing the inflatable mask to the distal end of the flexible breathing tube, said mask contoured to the anatomy of the oropharynx region of the throat;

The provision of the aforementioned laryngeal mask which, includes a stiff support structure for the inflatable mask formed by the distal end of the breathing tube, and a contoured rear surface on the inflatable mask, both aiding in the insertion and positioning of the device within the oropharynx;

The provision of the aforementioned laryngeal mask which, includes a perforated extension of the flexible breathing tube within the inflatable mask portion so as to provide alternate airways in the event the distal lumen is blocked;

The provision of the aforementioned laryngeal mask which, includes a flexible breathing tube having an elliptical cross-section, composed of a deformable, low friction material so as to permit the passage of large diameter endo-tracheal tubes and related medical instruments;

The provision of the aforementioned laryngeal mask, which includes an endo-tracheal tube retainer for use in conjunction with the laryngeal mask and endo-tracheal tubes, the endo-tracheal tube retainer facilitating the removal of the laryngeal mask from a patient's oropharynx without the accidental displacement of any inserted endo-tracheal tubes; and The provision of the aforementioned laryngeal mask which includes an endo-tracheal tube retainer, which may also be placed in a patient's oropharynx and serve as an intubating stylet.

Briefly stated, the removable laryngeal mask of the present invention is primarily intended to facilitate lung ventilation and the insertion of endo-tracheal tubes or related medical instruments into a patient's trachea as needed during general anesthesia, intensive care, or critical patient care. The removable laryngeal mask comprises a flexible ventilation tube and an inflatable positioning shield conforming to the anatomy of the oropharynx region surrounding the laryngeal opening, and securely affixed to the distal end of the ventilation tube. A separate endo-tracheal tube retainer facilitates removal of the laryngeal mask from the patient's oropharynx without dislodging any endotracheal tubes or related medical instruments passing through the laryngeal mask into the patient's trachea.

The flexible ventilation tube of the laryngeal mask is gently curved along an arc approximating the curvature of the passage from a patient's oral cavity to the laryngeal region. The ventilation tube is of sufficient length that the tube terminates exterior to the oral cavity after proper insertion and positioning of the laryngeal mask, thereby allowing endo-tracheal tubes and related medical devices to be easily inserted or attached. The ventilation tube is composed of a low-friction elastic plastic polymer, and has an elliptical cross section closely conforming to the actual cross section of the human throat. Large diameter endo-tracheal tubes and related medical instruments may pass freely through the flexible ventilation tube due to the low friction nature of the plastic polymer and the ability of the tube to deform to accommodate the larger diameter medical instruments. Passing through the rear portion of the inflatable positioning shield, the flexible ventilation tube terminates at an angle to the length of the tube, creating an elongated distal lumen open to the front recess of the inflatable positioning shield. The elongated distal portion of the ventilation tube forming the distal lumen serves the additional function of providing a semi-rigid substructure onto which the inflatable positioning shield is secured.

In addition to the elongated elliptical distal lumen, the peripheral surface of the flexible ventilation tube distal end contains numerous auxiliary ventilation lumen open to the front recess of the inflatable positioning shield. These auxiliary ventilation lumens function to provide alternate air passageways in the event the primary distal lumen becomes obstructed during the use of the laryngeal mask. Airflow through the auxiliary ventilation lumen prevents the formation of a pressure gradient between the ventilation tube and the front recess, thereby preventing any obstructing material from becoming lodged within the distal lumen.

Secured to the elongated distal portion of the flexible ventilation tube by an air-tight seal, the inflatable positioning shield serves to secure the laryngeal mask within a patient's oropharynx, adjacent the tracheal opening. The inflatable positioning shield is composed of an inflatable annular toroid, a recessed front cavity, and several semi-rigid structures molded to fit the anatomy of the laryngeal region. During insertion of the laryngeal mask, the inflatable annular toroid is deflated, reducing the overall size of the laryngeal mask and facilitating proper insertion. Upon positioning adjacent the laryngeal opening, the annular toroid is inflated by means of an externally connected air passage, conforming to the actual and potential space surrounding the rear and peripheral portions of the ventilation tube distal lumen. The inflated annular toroid exerts pressure against the structures of the oropharynx, forming a tightly sealed recessed front cavity surrounding the elongated elliptical distal lumen and the laryngeal opening. A pair of raised longitudinal ridges on the rear surface of the inflatable positioning shield and a frontal notch conforming to the tracheal anatomy further serve to aid in maintaining proper positioning of the laryngeal mask after inflation by preventing lateral movement within the oropharynx cavity. The ridges also facilitate placement by reducing drag.

Upon proper inflation, endo-tracheal tubes and related medical devices passing through the flexible ventilation tube exit the elongated distal lumen axially aligned for entry into the laryngeal opening. Removal of the laryngeal mask from the oropharynx may be accomplished without dislodging any inserted endo-tracheal tubes or related medical devices with the aid of an endo-tracheal tube retaining device. The retaining device, composed of a narrow semi-rigid rod with a softer and pliable cap at one end and a tapered connection adapter at the other, is inserted through the laryngeal mask into the proximal end of an endo-tracheal tube until the tapered connection adapter is securely fitted within the tube. As the laryngeal mask is withdrawn from the patient's oropharynx, the endo-tracheal tube retaining device maintains the proper positioning of the endo-tracheal tube by allowing a restraining force to be exerted counter to the friction force associated with the withdrawal of the laryngeal mask. Once clear of the oral cavity, the laryngeal mask is slipped off the proximal end of the endo-tracheal tube retaining device, allowing the endo-tracheal tube or related medical instrument to remain properly positioned within the larynx. Finally, the semi-rigid rod of the endotracheal tube retaining device can also be used as an intubating stylet for any further medical devices, which need to be passed through the oropharynx and into the inserted endo-tracheal tube after removal of the laryngeal mask. Of course, the rod can also be used separately as an intubating stylet for direct visualization.

These and other objects and advantages of the present invention will become more apparent from the description that follows.

BRIEF DESCRIPTION OF THE DRAWINGS

In the drawings, FIG. 1 is a top view of the laryngeal mask of the present invention illustrating the flexible breathing tube and the inflatable positioning shield;

FIG. 1A is a cross-sectional view taken along line 1A—1A in FIG. 1;

FIG. 2 is a side view of the inflatable positioning shield after inflation;

FIG. 3 is a sectional view of the inflatable positioning shield after inflation, taken along line 3—3 of FIG. 1;

FIG. 8 is a plan view of the endo-tracheal tube retainer, illustrating the soft cap portion;

FIG. 9 is a plan view of the endo-tracheal tube retainer, illustrating the separation of the tube retainer body from the connection adapter;

FIG. 10 is a front view of the distal end of the connection adapters, taken along line 10—10 of FIG. 9, illustrating the air-flow grooves;

FIG. 11 is a plan view of the laryngeal mask of the present invention during use, showing interaction with an endo-tracheal tube and the endo-tracheal tube retainer;

FIG. 12 is a plan view of endo-tracheal tube retainer during use, illustrating proper position of the tube retainer within an endo-tracheal tube; and FIG. 13 is a plan view of the laryngeal mask of the present invention during removal, illustrating the operation of the endo-tracheal tube retainer.

Corresponding reference numerals will be used throughout the several figures of the drawings.

DESCRIPTION OF THE PREFERRED EMBODIMENTS

The following detailed description illustrates the invention by way of example and not by way of limitation. The description will clearly enable one skilled in the art to make and use the invention, describes several embodiments, adaptations, variations, alternatives, and uses of the invention, including what we presently believe is the best mode of carrying out the invention.

Figure 7:
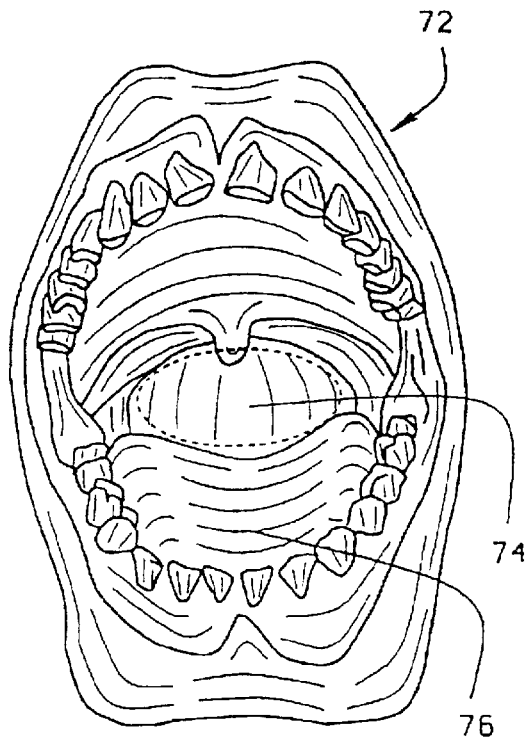
FIG. 7 is an artists rendition of a patient's oral cavity, illustrating the elliptical nature of the opening into the oropharynx region.

Referring to the drawings, and particularly FIGS. 1–3 inclusive, the removable laryngeal mask of the present invention is shown generally at 20. The laryngeal mask 20 comprises an inflatable positioning shield 22 secured to the distal end 24 of a respiratory tube 26, forming a smooth arcuate curve as shown in FIG. 3. Composed of a flexible silicone-rubber polymer, respiratory tube 26 has an elliptical cross-section (see FIG. 1A), approximating, for ease of insertion, the shape of the human throat shown in FIG. 7. Capable of spreading radially, respiratory tube 26 can accommodate the passage of cuffed endo-tracheal tubes and related medical devices up to 8.0 French in diameter. The length of respiratory tube 26 is such that when the laryngeal mask 20 is properly positioned for use within the oropharynx, the attachment end 28 of respiratory tube 26 is located exterior to the oral cavity. The attachment end 28 of the respiratory tube 26 terminates in an unobstructed proximal lumen 30, providing a direct pathway through the respiratory tube 26 to the distal end 24 and distal lumen 32. In alternative embodiments, the attachment end 28 may be fitted with adapters or connectors (not shown) suitable for connection to a variety of medical devices, for example, lung ventilation machines.

The distal end 24 is the continuous portion of respiratory tube 26 which has passed through an airtight peripheral seal 34 at the rear of the inflatable positioning shield 22, and into the shield recess 36. The distal end 24 terminates at an angle to its length, forming the elongated elliptically shaped distal lumen 32 open to the interior of the shield recess 36. The elongated lower surface of the distal end forms the shield support 37, and provides a semi-rigid structure onto which the positioning shield 22 is secured. Numerous ventilation lumen 38 perforate the distal end 24 to provide alternate airways in the event the distal lumen 32 becomes obstructed during patient lung ventilation. The ventilation lumen 38 prevent the formation of a pressure differential between the shield recess 36 and flexible respiratory tube 26. Absent a pressure differential, any object obstructing the distal lumen 32 will not become inextricably lodged within the distal end 24.

Figure 5:
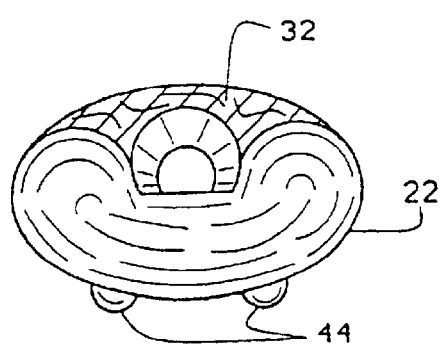
FIG. 5 is a sectional view of the inflatable positioning shield after inflation, taken along line 5—5 of FIG. 4, illustrating the recessed front of the positioning shield and the unobstructed distal lumen of the flexible breathing tube.
Figure 6:
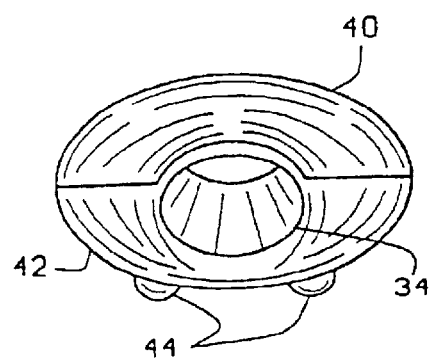
FIG. 6 is a rear view of the inflatable positioning shield after inflation, with the flexible breathing tube removed.
Figure 4:
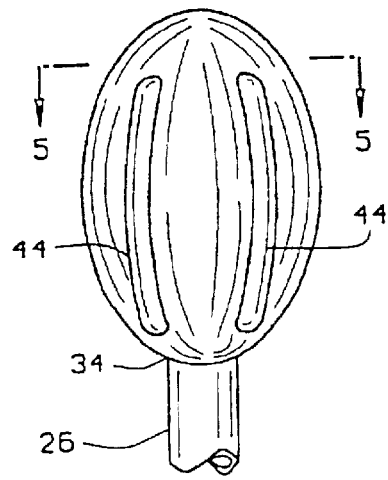
FIG. 4 is bottom view of the inflatable positioning shield.

The inflatable positioning shield 22 is composed of a wedge-shaped toroid 40, and a pliable molded posterior base 42. Inflation of the toroid 40 is accomplished by means of a conventional inflation device (not shown), forming an ovoid shape conforming to the approximate available space in the oropharynx region. The posterior base is secured longitudinally in an airtight manner to the lower surface of the shield support 37. The posterior base 42 forms an elongated and tapered hemisphere, best seen in FIGS. 2–4. Two semi-rigid raised runners 44 formed of molded silicone rubber are positioned longitudinally parallel to each other along the lower surface of the posterior base 42. During insertion of the laryngeal mask 20, the raised runners 44 guide the placement of the inflatable positioning shield 22, aid in preventing lateral movement by fitting to the rear anatomy of the oropharynx region, and facilitate placement by decreasing drag. In fluid communication with the posterior base 42, the annular toroid 40 is secured to the peripheral upper surface of the posterior base 42, and inflates simultaneously to form the shield recess 36. A tracheal notch 46 is formed in the portion of the annular toroid 40 traversing the front of the inflatable positioning shield 22, best seen in FIG. 1. The tracheal notch 46 surrounds the trachea after proper positioning and inflation of the laryngeal mask 20, preventing lateral movement and creating a better air-tight fit with the trachea.

During use, the laryngeal mask 20 is inserted through the oral cavity with the annular toroid 40 fully deflated. The smooth arcuate curve of the combined respiratory tube 26 and positioning shield 22 ensures proper positioning of the laryngeal mask 20 within the anatomy surrounding the laryngeal opening. Upon proper positioning, as determined by a resistance to further forward motion, the annular toroid 40 is inflated as described above. When fully inflated, the annular toroid 40 exerts sufficient pressure against the structures of the oropharynx to form a tight seal surrounding the laryngeal opening. Positioned within the shield recess 36, the distal lumen 32 is axially aligned with the laryngeal opening, permitting positive lung ventilation to be performed, or allowing endotracheal tubes or related medical instruments inserted through the respiratory tube 26 to exit the distal lumen 32 is directly aligned for passage into the laryngeal opening.

Removal of the laryngeal mask 20 is normally the reverse of the insertion procedure described above. In some situations, however, it is desired to remove the laryngeal mask 20 without simultaneously removing or dislodging endo-tracheal tubes or related medical devices passing through respiratory tube 26 into the laryngeal opening. Referring generally to FIGS. 8–13, removal of the laryngeal mask 20 under such circumstances is facilitated by means of a tube retainer, shown generally at 48.

Tube retainer 48 comprises a connection adapter 50, a stylet rod 52, and an endcap 66 Connection adapter 50 is composed of a soft semi-rigid material forming a truncated conical structure having four equidistantly positioned longitudinal ventilation grooves 56. Each ventilation groove 56 permits the passage of air around the connection adapter 50 after insertion within an endotracheal tube as shown generally in FIGS. 11–13. The exterior surface of connection adapter 50 between each ventilation groove 56 is threaded with threads 60. Each thread 60 is angled and shaped so as to facilitate insertion of the connection adapter 50 into an endo-tracheal tube by means of a longitudinally directed force applied to the adapter, but to exert a resistive force against the removal of connection adapter 50 from an endo-tracheal tube in opposition to an oppositely directed longitudinally applied force. Alternatively, the adapter may be screwed into place, and unscrewed, as desired. The conical nature of the connection adapter 50 permits the tube retainer 48 to fit securely within the opening of a variety of endo-tracheal tubes, ranging from standard size No. 6 through standard size No. 8 tubes. The present invention may be adapted as desired to accommodate larger and/or smaller tubes without departing from the scope of the present invention. As the tube retainer 48 is inserted within the opening of an endo-tracheal tube, the increasing exterior diameter of the connection adapter 50 prevents insertion beyond a certain point, limited by the interior diameter 64 of the endo-tracheal tube.

The connection adapter 50 is secured at its base to a disk-shaped adapter base 62. Stylet rod 52 is a semi-rigid, circular cross-section rod. The length of stylet rod 52 is sufficient to traverse the distance between a point external to a patient's oral cavity and the laryngeal opening. During the insertion of the rod retainer 48 within an endo-tracheal tube or related medical instrument, the end of stylet rod 52, external to the oral cavity, consists of a softer stylet cap 66. Of course, rod 52 may be used separately as an intubating stylet for direct visualization by unscrewing connector adapter 50 from rod 52 and placing cap 66 into the trachea directly. The soft cap 66 is designed and configured to reduce potential tracheal trauma when used as an intubating stylet.

FIGS. 11–13 illustrate the use of the tube retainer 48 during removal of an laryngeal mask 20. As described above, the use of a tube retainer 48 prevents the displacement of any inserted endo-tracheal tubes during removal of the laryngeal mask 20. The connection adapter 50 of tube retainer 48 is secured to the stylet rod 52 and passed through the respiratory tube 26. The connection adapter 50 partially enters the proximal opening of the inserted endo-tracheal tube 70 as shown in FIG. 11. The length of the stylet rod 52 is sufficient to extend beyond the oral cavity after insertion within the endo-tracheal tube 70, allowing manipulation of the tube retainer as needed to ensure a secure insertion. As shown in FIG. 13, the laryngeal mask 20, may then be removed from the oropharynx without dislodging the endo-tracheal tube 70 by sliding the laryngeal mask 20 along the tube retainer 48. Tube retainer 48 allows force to be exerted through the stylet rod 52 and connection adapter 50 on the endo-tracheal tube 70, resisting the tendency of the endo-tracheal tube 70 to withdraw from the laryngeal opening as the laryngeal mask 20 is removed. Once clear of the oral cavity, the laryngeal mask 20 is simply slid over the stylet cap 66 on the tube retainer 48, allowing the endo-tracheal tube to remain in place within the patient's laryngeal opening. The stylet is then removed by unscrewing it from the endo-tracheal tube.

In view of the above, it will be seen that all the objects and features of the present invention are achieved, and other advantageous results obtained. The description of the invention contained herein is illustrative only, and is not intended in a limiting sense.

What is claimed is:

1. A method for removing an inflatable laryngeal mask from a patient without dislodging any inserted endotracheal tubes or related medical instruments into the patient's laryngeal opening by using a tube retaining device, the method comprising the steps of:

inserting the tube retaining device through an opening in the inflatable laryngeal mask exterior to the oral cavity;

securing the tube retaining device within a proximal end of the previously inserted endo-tracheal tube within said inflatable laryngeal mask;

deflating said inflatable laryngeal mask;

simultaneously withdrawing said deflated inflatable laryngeal mask from the patient's oral cavity and exerting a retaining force on the tube retaining device sufficient to prevent friction from dislodging said endo-tracheal tube; and sliding the inflatable laryngeal mask off the proximal end of said retaining device.

2. A method for removing an inflatable laryngeal mask from a patient without dislodging any inserted endo-tracheal tubes or related medical instruments into the patient's laryngeal opening by using a tube retaining device, the method comprising the steps of:

securing the tube retaining device within a proximal end of an endotracheal tube;

inserting the endotracheal tube through an opening in the inflatable laryngeal mask;

removing said inflatable laryngeal mask by withdrawing said inflatable laryngeal mask from the patient's oral cavity and exerting a retaining force on the tube retaining device sufficient to prevent friction from dislodging said endo-tracheal tube; and removing the inflatable laryngeal mask.

3. The method of claim 2 wherein removing the inflatable laryngeal mask comprises separating the tube retaining device from the endotracheal tube and sliding the inflatable laryngeal mask off an end of the tube retaining device.

4. The method of claim 2 wherein removing the inflatable laryngeal mask comprises sliding the inflatable laryngeal mask off a proximal end of the tube retaining device.

5. A method for removing an laryngeal mask from a patient without dislodging any inserted endo-tracheal tubes or related medical instruments into the patient's laryngeal opening by using a tube retaining device, the method comprising the steps of:

inserting an endotracheal tube through an opening in the laryngeal mask;

securing the tube retaining device within the endotracheal tube;

removing the laryngeal mask by withdrawing the laryngeal mask from the patient's oral cavity and exerting a force on the tube retaining device sufficient to prevent dislodging the endo-tracheal tube; and removing the laryngeal mask.

6. The method of claim 5 wherein removing the laryngeal mask comprises separating the tube retaining device from the endotracheal tube and sliding the laryngeal mask off an end of the tube retaining device.

7. The method of claim 5 wherein removing the laryngeal mask comprises sliding the laryngeal mask off a proximal end of the tube retaining device.

8. A method for removing a laryngeal airway from a patient's oral cavity without dislodging any inserted endotracheal tubes or related medical instruments into the patient's laryngeal opening by using a tube retaining device, the method comprising the steps of:

securing the tube retaining device within a proximal end of an endotracheal tube;

inserting the endotracheal tube through the laryngeal opening;

removing the laryngeal airway by withdrawing the laryngeal airway from the patient's oral cavity and exerting a retaining force on the tube retaining device, the retaining force being sufficient to prevent friction from dislodging said endo-tracheal tube; and removing the laryngeal airway.

* * * * *